United States Patent [19]

Serwer et al.

[11] Patent Number: 5,185,071
[45] Date of Patent: Feb. 9, 1993

[54] PROGRAMMABLE ELECTROPHORESIS WITH INTEGRATED AND MULTIPLEXED CONTROL

[75] Inventors: Philip Serwer; Frederick J. Dunn, both of San Antonio, Tex.

[73] Assignee: Board of Regents, The University of Texas System, Austin, Tex.

[21] Appl. No.: 605,796

[22] Filed: Oct. 30, 1990

[51] Int. Cl.$^5$ .................... G01N 27/26; B01D 57/02
[52] U.S. Cl. ............................ 204/299 R; 204/182.8; 204/182.1
[58] Field of Search .............. 204/299 R, 182.8, 182.1

[56] References Cited

U.S. PATENT DOCUMENTS

| | | | |
|---|---|---|---|
| 2,648,636 | 8/1953 | Ellis et al. | 252/303 |
| 2,992,979 | 7/1961 | Magnuson et al. | 204/182.7 |
| 3,567,611 | 9/1968 | Michel et al. | 204/182.8 |
| 3,677,930 | 7/1972 | Meshbane et al. | 204/299 R |
| 3,865,712 | 2/1975 | Davies | 204/299 R |
| 3,888,759 | 6/1975 | Elson et al. | 204/299 R |
| 3,930,973 | 1/1976 | Nerenberg | 204/182.7 |
| 3,988,230 | 10/1976 | Krotz | 204/182.1 |
| 4,040,940 | 9/1977 | Bier | 204/299 R |
| 4,061,561 | 12/1977 | Fletcher et al. | 204/299 R |
| 4,088,561 | 5/1978 | Anderson | 204/299 R |
| 4,148,703 | 4/1979 | Trop et al. | 204/182.1 |
| 4,294,684 | 10/1981 | Serwer | 204/299 R |
| 4,305,799 | 12/1981 | Scharz et al. | 204/182.1 |
| 4,385,974 | 5/1983 | Schevtz | 204/182.1 |
| 4,432,849 | 2/1984 | Saito | 204/180.1 |
| 4,569,741 | 2/1986 | Pohl | 204/186 |
| 4,624,768 | 11/1986 | Yoshida et al. | 204/182.8 X |
| 4,693,804 | 9/1987 | Serwer | 204/182.1 |
| 4,886,589 | 12/1989 | Southern | 204/182.8 |
| 4,898,658 | 2/1990 | Karger et al. | 204/299 R |
| 4,909,920 | 3/1990 | Sarrine et al. | 204/299 R |
| 4,911,817 | 3/1990 | Kindlman | 204/299 R |
| 4,980,247 | 12/1989 | Sarrine et al. | 364/571.04 |

FOREIGN PATENT DOCUMENTS 0105012 12/1981 Japan .
PCT/US83/-
 01826 11/1983 World Int. Prop. O. .
PCT/GB86/-
 00578 9/1986 World Int. Prop. O. .

OTHER PUBLICATIONS

Volker Gekeler et al., "Computer-Controlled Discontinuous Rotating Gel Electrophoresis for Separation of Very Large DNA Molecules 38 Analytical Biochemistry 181 (Sep. 1989) 227-233.
Chemical Abstracts 111(17): 149719, Amano & Tsutsumi & Construction of an apparatus of high resolvability for rotating field electrophoresis of multisamples" Tanpakushitsu Kakusau Koso, 34(8) (1989).
Southern et al.–"A Model for the Separation of Large DNA Molecules by Crossed Field Gel Electrophoresis," Nucleic. Acids Res. 15(15):5925-5943, 1987.

(List continued on next page.)

*Primary Examiner*—John Niebling
*Assistant Examiner*—John S. Stavsiak
*Attorney, Agent, or Firm*—Arnold, White & Durkee

[57] ABSTRACT

A user programmable device for horizontal gel eletrophoresis is provided. This device can both accurately and programmably control: (a) the angle between electrical field and gel by use of a rotatable gel bed, (b) magnitude of the electrical field, and (c) temperature. The present invention is programmable by a microprocessor-based contol board which sends control signals to: (a) a motor attached to the rotatable gel (b) the source of elecrical potential and (c) Peltier devices attached to the sides of buffer chambers horizontally displaced from the rotatable gel bed. The present invention is particularly appropriate for lowering cost, lowering footprint, reducing heat dissipated, maintaining close tolerances of electric field gradients and temperature, and exploring and using thus far untried modes of electrical field variation. It is thereby suitable for analyzing large linear DNA, open circular DNA and/or DNA-protein complexes. Control of several disks, power supplies and temperature cells by one control board (multiplexing) is an option.

15 Claims, 3 Drawing Sheets

OTHER PUBLICATIONS

Serwer–"The Mechanism of DNA's Fractionation During Pulsed–Field Agarose Gel Electrophoresis: A Hypothesis," *Applied and Theoretical Electrophoresis* 1:000–000, 1988.

Serwer–"Use of Gel Electrophoresis to Characterize Multi–Molecular Aggregates," *Methods in Enzymology* 130:116–132, 1986.

Anand–"Pulse Field Gel Electrophoresis: A Technique for Fractionating Large Dan Molecules," *Trends in Genetics* 2(11):278–283, 1986.

Serwer–"Gel Electrophoresis with Discontinuous Rotation of the Gel: An Alternative to Gel Electrophoresis with Changing Direction of the Electric Field," *Electrophoresis* 8:301–304, 1987.

Serwer–"The Mechanism of DNA's Fractionation During Pulsed–Field Agarose Gel Electrophoresis: A Hypothesis," *Applied and Theoretical Electrophoresis* 1:19–22, 1988.

Gemmill, et al.–"Construction of Long–Range Restriction Maps in Human DNA Using Pulsed Field Gel Electrophoresis," *Gene Anal Techn* 4:119–131, 1987.

Gardiner, et al.–"Fractionation of Large Mammalian DNA Restriction Fragments Using Vertical Pulsed– Field Gradient Gel Electrophoresis," *Somatic Cell and Molec. Genet.* 12(2):185–195, 1986.

Lai, et al.–"Pulsed–Field Gel Electrophoresis," *BioTechniques* 7(1):34–42, 1989.

Clark et al.–"A Novel Instrument for Separating Large DNA Molecules with Pulsed Homogeneous Electric Fields," *Science* 241:1203–1205, 1988.

Cantor, et al.–"Pulsed–Field Gel Electrophoresis of Very large DNA Molecules," *Ann. Rev. Biophys. Chem.* 17:287–304, 1988.

Sutherland, et al.–"Separation of Chromosomal Link DNA Molecules: Pneumatic Apparatus for Rotating Gels During Electrophoresis," *Electrophoresis* 10:315–317, 1989.

Louie, et al.–"A Hybrid Mode of Rotating Gel Electrophoresis for Separating Linear and Circular Duplex DNA," *Applied and Theoretical Electrophoresis* 1:169–173, 1989.

Serwer–"Sieving by Agarose Gels and its Use During Pulsed–Field Electrophoresis," *Biotech. and Genet. Eng. Rev.* 8:319–343, 1990.

Lane, et al.–"Quantized Viral DNA Packaging Revealed by Rotating Gel Electrophoresis," *Virology* 174:472–478, 1990.

Mathew, et al.–"High–Resolution Separation and Accurate Size Determination in Pulsed–Field Gel Electrophoresis of DNA," *Biochemistry* 27:9204–9210, 1988.

Cantor, et al.–"High–Resolution Separation and Accurate Size Determination in Pulsed–Field Gel Electrophoresis of DNA," *Biochemistry* 27:9216–9221, 1988.

Lalande, et al.–"Pulsed Field Elecrophoresis: Application of the Computer Model to the Separation of Large DNA Molecules," *Proc. Natl. Acad. Sci. USA* 84:8011–8015, 1987.

Birren, et al.–"Pulsed Field Gel Electrophoresis: Studies of DNA Migration Made with the Programmable, Autonomously Controlled Electrode Electrophoresis System," *Electrophoresis* 10:302–309, 1989.

Vollrath, et al.–"Resolution of DNA Molecules Greater than Five Magabases by Contour–Clamped Homogeneous Electric Fields," *Nucleic Acids Research* 15(19):7865–7876, 1987.

Chu–"Pulsed Field Electrophoresis in Contour– Clamped Homogeneous Electric Fields for the Resolution of DNA by Size or Topography," *Electrophoresis* 10:290–295, 1989.

Serwer, et al.–"Role of Gene 6 Exonuclease in the Replication and Packaging of Bacteriophage T7 DNA," *J. Mol. Biol.* 215:287–299, 1990.

Turmel, et al.–"Molecular D Trapping and Band Narrowing with High Frequency Modulation of Pulsed Field Electrophoresis," *Nucleic Acids Research* 18(3):569–575, 1989.

Serwer, et al.–"Electrophoresis of Bacteriophage T7 and T7 Capsids in Agarose Gels," *J. Virology* 28(3):917–928, 1978.

Olson–"Pulsed–Field Gel Electrophoresis," 183–227, nd.

Smith, et al.–"Purification, Specific Fragmentation and Separation of Large DNA Molecules," *Methods in Enzymology* 155:449–467, 1987.

Fuke, et al.–"Isolation of Open–Circular DNA Molecules by Retention of Agar Gels," *J. Mol. Biol.* 52:395–397, 1970.

(List continued on next page.)

OTHER PUBLICATIONS

Borejvo, et al.–"Electrophoresis and Orientation of F-Actin in Agarose Gels," *Biophys. J.* 56:285-293, 1989.

Chu, et al.–"Separation of Large DNA Molecules by Contour-Clamped Homogeneous Electric Fields," *Science* 234:1582, 1986.

Carle, et al.–"Electrophoretic Separation of Large DNA Molecules by Periodic Conversion of the Electric Field," *Science* 232:65-69, 1986.

Cantor, et al.–"Voltage Ramp Pulsed Field Gel Electrophoresis Separation of Large DNA Molecules," *Electrophoresis of nucleic acids* 161-171, 1986.

Carle, et al.–"Separation of Chromosomal DNA Molecules from Yeast by Orthogonal-Field-Alternation Gel Electrophoresis," *Nucleic Acids Research* 12(14):5647-5664, 1984.

Stellwagen, et al.–"Gel Electrophoresis of DNA," *Proceedings Report* 104-138, 1986 Meeting of the Americas Branch of the Electrophoresis Society, Mar. 26-28, 1986.

Schwartz, et al.–"Separation of Yeast Chromosome-Sized DNA by Pulsed Field Gradient Gel Electrophoresis," *Cell* 37:67-75, 1984.

Serwer–"Electrophoresis of Duplex Deoxyribonucleic Acid in Multiple-Concentration Agarose Gels: Fractionization of Molecules with Molecular Weights Between $2 \times 10^6$ and $110 \times 10^6$, *Biochemistry* 19:3001-3004, 1980.

Hayward–"Unique Double-Stranded Fragments of Bacteriophage T5 DNA Resulting from Preferential Shear-Induced Breakage at Nicks," *Proc. Natl. Acad. Sci. USA* 71(5):2108-2112, 1974.

Lishanskaya, et al.–"Size Dependent Separation of High Molecular Weight Double-Stranded DNA by Means of Gel Electrophoresis," *Biochem. and Biophys. Res. Com.* 52(4):1213-1220, 1973.

Serwer, et al.–"Stability in In Vitro DNA Packaging of Bacteriophages: Effects of Dextrans, Sugars and Polyols," *J. Virology* 45(2):665-671, 1983.

McDonell, et al.–"Analysis of Restrictin Fragments of T7 DNA in Determination of Molecular Weights by Electrophoresis in Neutral and Alkaline Gels," *J. Mol. Biol.* 110:119-146, 1977.

Fangman–"Separation of Very Large DNA Molecules by Gel Electrophoresis," *Nucleic Acids Research*, 5(3):653-664, 1978.

Schwartz, et al.–"New Techniques for Purifying Large DNAs in Studying their Properties and Packaging," 189-195, nd.

Son, et al.–"Concatemerization and Packaging of Bacteriophage T7 DNA in Vitro: Determination of the Concatemers Link and Parents Kinetics by Use of Rotating Gel Electrophoresis," *Virology* 162:38-36, 1988.

Serwer, et al.–"Concatemers in a Rapidly Sedimenting, Replicating Bacteriophage T7 DNA," *Virology* 123:474-479, 1982.

Griess, et al.–"The Sieving of Rod-Shaped Viruses During Agarose Gel Electrophoresis," *Biopolymers* 29:1277-1287, 1990.

Adam, et al.–"Sheer Degradation of DNA," *Nucleic Acids Research* 4(4):1513-1537, 1977.

PROGRAMMABLE ELECTROPHORESIS WITH INTEGRATED AND MULTIPLEXED CONTROL

BACKGROUND OF THE INVENTION

The invention relates to a device and method for programmably controlling electrophoresis performed by use of either invariant or variable (pulsed) fields. More specifically, the present invention is directed toward a programmable control of the direction and magnitude of the electrical field experienced by a particle in a rotatable gel bed. The temperature of the gel bed and sample particles placed therein is also programmably regulated through a thermoelectric chilling device such as a Peltier device. The invention utilizes a user-programmable control board for multiplexing the control of both electric field (magnitude and direction) and temperature during either pulsed field gel (PFG) or invariant field gel electrophoresis. By programming the various conditions that determine the electrophoretic fractionation, the present invention increases the significance and usefulness of electrophoretic analysis of various complex particles such as proteins, peptides, or nucleic acids.

By far the most common method of analyzing particles, such as DNA molecules, is electrophoresis. Molecules or particles having net electrical charges may be analyzed by observing their migration in a gel subjected to the application of electrical fields. The migrations are dependent upon many factors which include but are not limited to the nature of electric fields, the pH of solvents containing the particles, the temperature of the solvent and the characteristics of the particles themselves. By changing the direction and magnitude of the electric field during electrophoresis, the length of DNA molecules which are separable has been increased to between 3.0–6.0 Mb. Thus, changing the direction of electrical field impinging upon the particles and/or the pulse duration and magnitude of the electric field will produce increased separation of either large DNA molecules or, presumably, other particles forming either a random coil or a flexible rod. Changing the direction of the impinging electrical field is typically achieved by either changing the electrical potential on vertical electrodes or rotating the gel in which migratory DNA-type particles are placed. Contained both over and within the gel is an electrically conductive solvent which conducts electrical current that, in the case of a rotating gel, is driven by an electrical potential from electrodes horizontally displaced adjacent the rotating bed. As the bed and particles rotate about a fixed axis, the electrical field angle of incidence upon the particles changes.

Although changing the magnitude and direction of electric fields improves fractionation of larger linear or open-circular DNA particles, there still remains a limit as to the size of particles that can be analyzed. For linear DNA molecules having lengths that exceed 3.0–6.0 Mb, additional procedures are needed. Further, when DNA particles have branches or other types of irregular protrusions (such as proteins, for example), improved control of electrical potential gradient (direction and magnitude) and temperature is needed to fractionate the particle. Oftentimes, when fractionating large particles, it is necessary to increase electrical potential gradients by injecting more power into the electrophoretic device. Increased power causes heat build-up within and across the gel bed thereby adversely affecting electrophoresis readings. A fast and efficient way of dissipating heat away from the particles and gel bed is needed when migrating large particles using higher power input levels.

Not only are conventional devices unable to analyze large linear (>6 Mb) or open-circular (>0.3 Mb) DNA particles, but they also suffer from poor adaptability in analyzing different forms of particles. Each time a different DNA particle is sought for analysis, the apparatus must be changed or retrofitted to accommodate the particular size, shape or composition of that particle. For example, a smaller particle may respond poorly to discontinuous or continuous rotation of the gel bed during electrophoresis. In such a case, it may be desirable to provide unidirectional electrophoresis without changing or retrofitting the electrophoretic apparatus. Still further, it may even be desirable to provide more accurate readings when, for example, performing a highly resonant separation, i.e., one that has a steep dependance on parameters of electrophoresis. In such a case, uniformity and control of both electrical potential gradient and temperature is critical.

Perhaps the greatest difficulty when performing electrophoresis is to perform repetitive tests using the same electric field gradient and temperature for each test. Thus, a need arises for programmably and accurately controlling, preferably with programmable storage and recall, electrophoretic conditions. Furthermore, the electrophoretic device must have the capacity for accurate control during successive tests, such that the conditions remain constant for each test. Current devices are not known for their ability to control temperature and electrical potential; most do not store and recall control parameters for repetitive electrophoresis operations. Further, current devices do not multiplex control of two or more electrophoretic disks or electrophoretic devices, nor can current devices programmably control multiple modes of variation of the electrical field and other control parameters values, for example, a mode can be the temporal sequence of disk rotations and electrical source (magnitude and polarity).

SUMMARY OF THE INVENTION

Accordingly, it is desirable to provide an apparatus and method for programmably and accurately controlling electrophoresis and thereby overcome the problems outlined above. More importantly, it is desirable to provide an apparatus and method for controlling, with high resolution, multiple modes of control parameters such as electrical field (magnitude and direction) and temperature placed upon electrically migratory particles. The present invention is particularly appropriate for controlling electrophoretic migration of large linear or open-circular DNA particles or particles or varying sizes and shapes.

Broadly speaking, the present invention contemplates an apparatus for programmably controlling electrophoresis. This apparatus includes a planar, rotatable support for a medium in which one or more samples of particles to be separated can be placed. A containment means, which includes at least two buffer holding tanks, is used for containing a buffer solution upon the upper surface of the rotatable medium. The rotatable support and power supply connected to the containment means is controlled by a user-programmable means for controlling orientation of the disk, and the magnitude and polarity of electric field placed upon the particles. Further, the user programmable means includes a temperature control means connected to the containment means for controlling temperature of the buffer solution and particles during electrophoresis. The buffer solution contained across the upper surface of the rotatable medium is closely controlled such that the particles contained therein are subject to substantially precise electrical field and temperature. Precision is achieved by closely controlling all of the major conditions of electrophoresis. Furthermore, the major control modes can each be independently controlled such that, e.g., the power supply is controlled independent of the rotating means and independent of the temperature control means. Still, further, multiplexing means is provided which can programmably control multiple electrophoresis disks or devices of the present invention, each device independent of the other.

In one embodiment of the present invention, a power supply is connected to the containment means for producing a pulsed electric field across the buffer solution in response to input from the programmable control means. In an alternative embodiment, the power supply can produce a continuous electric field across the buffer solution. In either embodiment: (a) the power supply is connectable to an electrode placed in each buffer tank thereby causing electric field to travel between each tank and through the conductive buffer solution placed over the gel bed; and (b) the orientation of the disk is programmably controlled.

Temperature control is achieved by a thermoelectric chilling device which releases heat from the buffer solution in response to electrical input from the programmed control means. The chilling device may include, but is not limited to, a Peltier device.

The present invention provides an apparatus for programmably controlling an electrophoretic device. The device includes a planar rotatable support containing a horizontal gel bed containing one or more DNA particles. A programmable rotating means is provided for rotating the support. The rotating means includes a DC stepping motor mechanically coupled to the support, a home finder disk also mechanically coupled to the support, and a control board electrically connected to the motor and disk for controlling the speed, direction and duration of movement of the motor. The apparatus also includes at least two buffer holding tanks horizontally displaced from the rotatable gel bed. The tanks open at the top to provide electrically conductive buffer solution between the tanks and over the gel bed. A programmable means is connected to the holding tanks for controlling the magnitude and polarity of the electrical field placed between the tanks. The programmable controlling means includes an electrode placed in each holding tank and a control board electrically connected to each electrode. The control board transmits electrical signals which control the magnitude and duration of electrical energy supplied to each electrode.

In addition to the rotating means and field controlling means, the present device also includes a programmable temperature control means, such as Peltier means, connected to the holding tanks. The Peltier means regulates the temperature of the buffer solution contained within the tanks and across the gel bed. The Peltier means includes at least two holding tanks and may also include an electrically non-conductive, thermally conductive sheet placed over a hole formed in each tank. An aluminum plate may be attached to the thermally conductive sheet on the external surface of the tank. A Peltier cell is then coupled to the aluminum plate and an aluminum heat sink is connected to each cell. A control board is then electrically connected to each cell which, in response to an electrical input, causes heat transfer from the solution to the heat sink.

The control board used for controlling the rotating means, controlling means and Peltier means of the present invention is a microprocessor and memory-based controller with programmable pulse generator. The control board, connected to the motor and disk is used for controlling the speed, direction and duration of movement of the motor in response to input from a computer. Further, the control board is also connected to each electrode and receives input for changing the magnitude, duration and polarity of electrical energy supplied to each electrode. Still further, the control board is also connected to each Peltier cell, and receives input from a temperature sensor and/or computer via a control board to input electrical energy to the cell which, in response to the electrical input expels heat from the solution. The present invention therefore provides an apparatus which can receive instructions and data from either a programmed computer output or from local memory to input controlling parameters upon the DNA particles. Such a controlling device thereby provides accurate programmable and repeatable test results—an improvement over conventional art.

The present invention also contemplates a method of multiplexing control of both electrical field and temperature during electrophoresis. In the method for multiplexing control, particles under study are placed onto a rotatable gel bed. A buffer solution is contained over the bed in communication with the particles. An electric field is then applied to the rotating bed causing varying angles of incidence in response to programmed input. Thermal energy can also be simultaneously either drawn from or added to the solution in response to programmed electrical input. The programmed electrical input, as mentioned above, includes a control board electrically connected to the buffer solution and connected to the rotating gel bed means. The control board functions to receive input from a computer or memory, and to transfer that input to controlling conditions that control or regulate the migration of the sample particles. Thus, the control board of the present invention offers independent control of electric field and temperature. Multiplexed control is also contemplated by the applicants to include control of multiple apparatuses: disks, Peltier devices and electric field (direction magnitudes and polarity) by use of a single control board. In one embodiment, more than one disk is placed in a single electrophoresis apparatus. Typically, the disks are placed in series, but may also be placed in parallel.

The present invention therefore provides a programmable controlling apparatus and method for closely regulating the electrical field placed across a rotating gel bed containing DNA particles. Further, the present invention regulates the temperature of solution placed over the gel bed and containing the particles. Both electrical field and temperature regulation are achieved either in conjunction or independent of each other during PFG electrophoresis. Still further, the present invention is user programmed from a remote computer and keyboard or from local/remote memory means available in a standard computer. The present invention additionally contemplates monitoring and correction of electric field and temperature in real-time. In addition, the present device is less expensive and space-consuming than electrophoretic control apparatus of conventional art.

DETAILED DESCRIPTION OF THE INVENTION

The Apparatus

Figure 1:
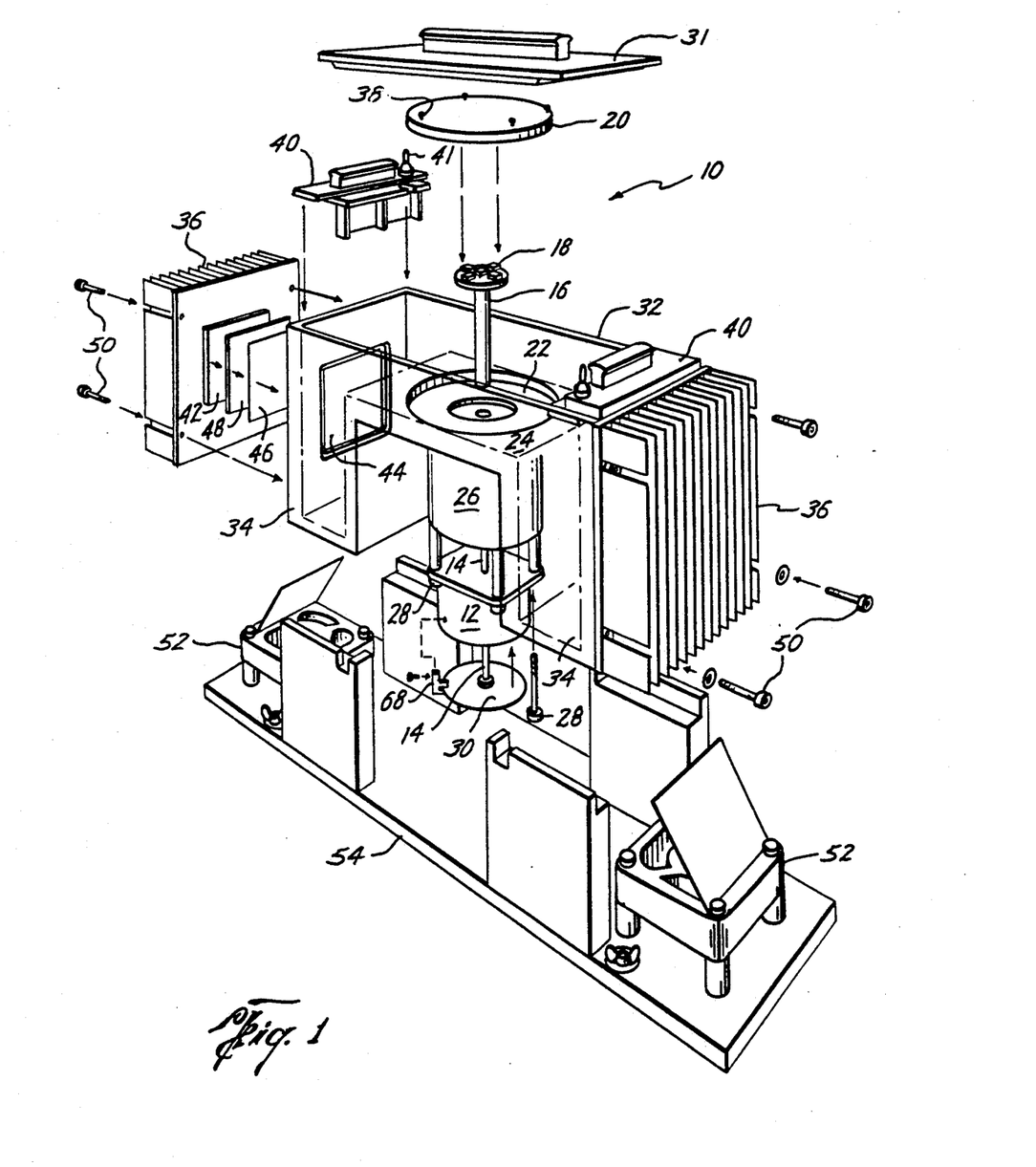
FIG. 1 is an exploded view of the apparatus of the present invention.

Referring to the drawings, FIG. 1 illustrates an electrophoretic apparatus or device 10. Device 10 comprises an apparatus designed for electrophoresis in horizontally submerged gels available, for example, from Aquebogue Machine and Repair Shop Aquebogue, New York, Model 850. To this apparatus is added a DC stepping motor 12 placed near the center of the device and having a vertically disposed shaft 14 attached thereto. Attachable to motor 12 at the opposite end from shaft 14 is a drive shaft 16 topped by a cross-shaped adapter pattern 18. Adapter pattern 18 includes protrusions arranged in a cross-shape configured to accommodate an engraved or indented pattern on the underneath side of disk 20 (not shown). Disk 20 functions to rotate according to rotational movement transferred from motor 12 through drive shaft 16. A suitable stepping motor 12 is provided by Superior Electric, Bristol, Conn., Model M061-FDO2E.

When assembled, disk 20 fits within trough 22 formed in raised platform 24. The depth of trough 22 accommodates the thickness of disk 20 such that when disk 20 is placed in trough 22, the upper surface of disk 20 is at the plane of the surface of raised platform 24.

Attached to the underneath side of platform 24 is casing 26. Casing 26 is preferably made of Plexiglass ®. Casing 26 surrounds shaft 14 between the underside of raised platform 24 and the top of assembly bolts 28 to prevent leakage of buffer solution placed above platform 24 and disk 20. Gaskets may be placed either upon drive shaft 16 or within casing 26. Motor 12, shaft 14 and home finder disk 30 are secured to casing 26 by bolts 28.

Surrounding platform 24 are containment walls 32. At opposing ends of containment wall 32 are buffer tanks 34 which have been made taller and thinner by a factor of two (15.2 cm × 15.9 cm wide is the preferred outer dimensions) than the buffer tanks used in most conventional devices. As will be discussed later, this modification was necessary to improve heat exchange through the tanks 34 to outer heat sinks 36. To provide structural stability and thermal insulation, all walls (Plexiglas ®), were thickened to approximately 0.5". The bed, while also made of Plexiglas ®, is preferably 1.0" thick. Also included is a lid 31 which resides over the containment wall 32 to prevent evaporation or dissipation of the solution and to slow heat exchange. Lid 31 also prevents contaminants from entering the gel bed either before, during or after electrophoresis.

Before electrophoresis, disk 20 must receive gels which are poured onto its upper surface. Gels can be poured directly onto the removable disk 20 outside of apparatus 10. Not shown in FIG. 1, is a ring having a beveled bottom and a diameter equal to that of disk 12, wherein the ring is placed on the upper surface of disk 12 in order to pour a gel within the apparatus of FIG. 1. Also not shown, is a well-forming comb supported in a position for casting a gel above the upper surface of disk 20. Molten gel or agarose is next poured inside the ring to a desired height upon disk 20. After gelation, the ring and comb are removed leaving a hardened gel with wells embedded therein. A discussion of gel casting techniques in bidimensional and rotating gel beds of the same invention are shown in U.S. Pat. No. 4,693,804 and U.S. patent Ser. No. 07/393,084, herein incorporated by reference.

Once the gels are cast and wells formed therein, sample particles which include proteins, peptides or nucleic acids are placed in the wells for electrophoretic study. It is important to note that, although proteins and nucleic acids are the preferred sample particles, any molecule or particle having electrical charges may migrate during electrophoresis, and, therefore, may be studied by device 10. U.S. Pat. No. 4,693,804, incorporated by reference herein, describes both particles which can be contained within the gels and buffers which can be placed over the gel bed.

It is important when loading the gel and particles upon disk 20 that the gel remains secure upon disk 20 after hardening. Further, when longer DNA molecules (greater than 0.1 Mb) are used, the particles must be protected from degradation caused by hydrodynamic shear. Presently, buffer solutions are usually made of either tris-acetate or tris-borate. It is contemplated that a phosphate buffer solvent would both minimize cost and maintain a physiological pH. Thus, a phosphate buffer may be substituted for the conventional acetate or borate buffers conventionally used. For long DNA particles, one way to prevent the degradation caused by hydrodynamic shear is to lyse the cells in gelled agarose plugs. Alternatively, if not embedded in plugs, the DNA molecules are handled by pipetting slowly in pipets having a 0.1 cm bore. Chromosomal DNA's as long as 1 or from 0.6 Mb have been successfully handled by this pipeting procedure.

Once the particles are, if necessary, pipeted upon the gel bed at well locations, buffer solution, such as acetate, borate or phosphate-based liquid, is placed over the bed and contained within walls 32. Large dimension buffer tanks 34 improve uniformity and control of both pH and temperature. During electrophoresis, motor 12 is activated and disk 20 responds by rotating. The gel bed and accompanying particles rotate upon disk 20 within the buffer solution.

An electrical field is placed across the rotating gel bed between electrodes 40 shown in FIG. 1 at the top of each buffer tank 34. The electrode assembly 40 is preferably made of Plexiglas ® and includes a receptor or banana plug 41 which receives electrical input either directly from a remote commercial power supply (not shown) or from a separate power control block 82. Preferably, platinum wires are used to make the connection from plug 41 to buffer tanks 34, however, other types of conductive wires are envisioned by the applicants. A current and electrical field is formed between electrodes 40 when the power supply is turned on, thereby causing an electric field across the rotating gel bed. As disk 20 rotates, the angle of incidence of electric field upon the sample particles changes. It is found that electrophoresis performed by an electric field which varies in either magnitude and direction (or both) causes improved fractionation of large DNA molecules (as long as 3-6 Mb for linear double-stranded DNA and 0.3 Mb for open circular DNA).

In addition to providing an electrical field that is user-programmable, the present invention also provides cooling of the solution which naturally warms when electric fields are transmitted therethrough. Device 10 is equipped with a thermoelectric chilling device or Peltier cell 42. Thermoelectric chilling of solution within tanks 34 is achieved through square holes 44 cut in the outside plates of both buffer tanks 34. Holes 44 are covered by an electrically non-conductive, thermally conductive sheet 46 secured to the external surface of each tank 34. Sheet 46 is preferably made of an alumina oxide ceramic made by Kyocera America, Inc., San Diego, Calif., Model A476. Exterior to sheet 46 is an aluminum plate 48, preferably 0.157 cm thickness added for structural stability. Peltier cell 42 is attached to the outer surface of plate 48 and receives current from an external, feedback regulated power supply. To assist the removal of the heat from the external side of Peltier cell 42, an aluminum heat sink 36, polished on its inner surface, is thermally coupled to cell 42. Heat sink 36 may be used, preferably made at Thermalloy, Inc., Dallas, Tex., Model 14288. Heat sink 36, cell 42, plate 48, sheet 46 are all held in place on the external surface of each buffer tank 34 by bolts 50 screwed into the side of buffer tanks 34. To assist in removal of heat from the heat sink, a fan 52 is mounted to base 54 of device 10. Each fan 52 blows air past heat sink 34 to discharge heat from the fins of heat sink 34 and into the outside environment.

Cooling of buffer solution is important for achieving accurate control of DNA migration. When no electrophoretic dissipation of heat occurs, the Peltier cooling procedure of FIG. 1 achieves a minimum temperature of 13°-14° C. below ambient temperature. This value changed to 10°-11° C., 7°-8° C. and 5°-6° C. when the electrophoretic power dissipation increased to 7.5, 15 and 25 watts, respectively.

Because of exposure of the electrically conductive heat sinks, at the outside of the apparatus 10, heat sinks 36 would become an electrical shock hazard if a leak from the apparatus brought them in contact with the buffer solution. Heat sinks 36 should, therefore, be carefully grounded and under no conditions should this ground be interrupted.

Peltier-cooled buffer tanks 34 function to suppress gradients of pH as well as suppressing temperature gradients within the buffer solution. Preferably, pH gradients are held below 0.005 pH units per cm. Temperature is maintained $< \pm 0.2°$ C. The improved control of pH and temperature yields improve control of electrical potential gradient between electrodes 40 of device 10. Thus, current drawn at constant electrical potential gradient may result in less than 2% variance during a 10-20 hour electrophoresis operation. The electrical potential gradient is measured by placing electrodes in the gel, a known distance apart. Accuracy of control of the above conditions of electrophoresis become more important as electrophoretic separations become more resonant.

Figure 2:
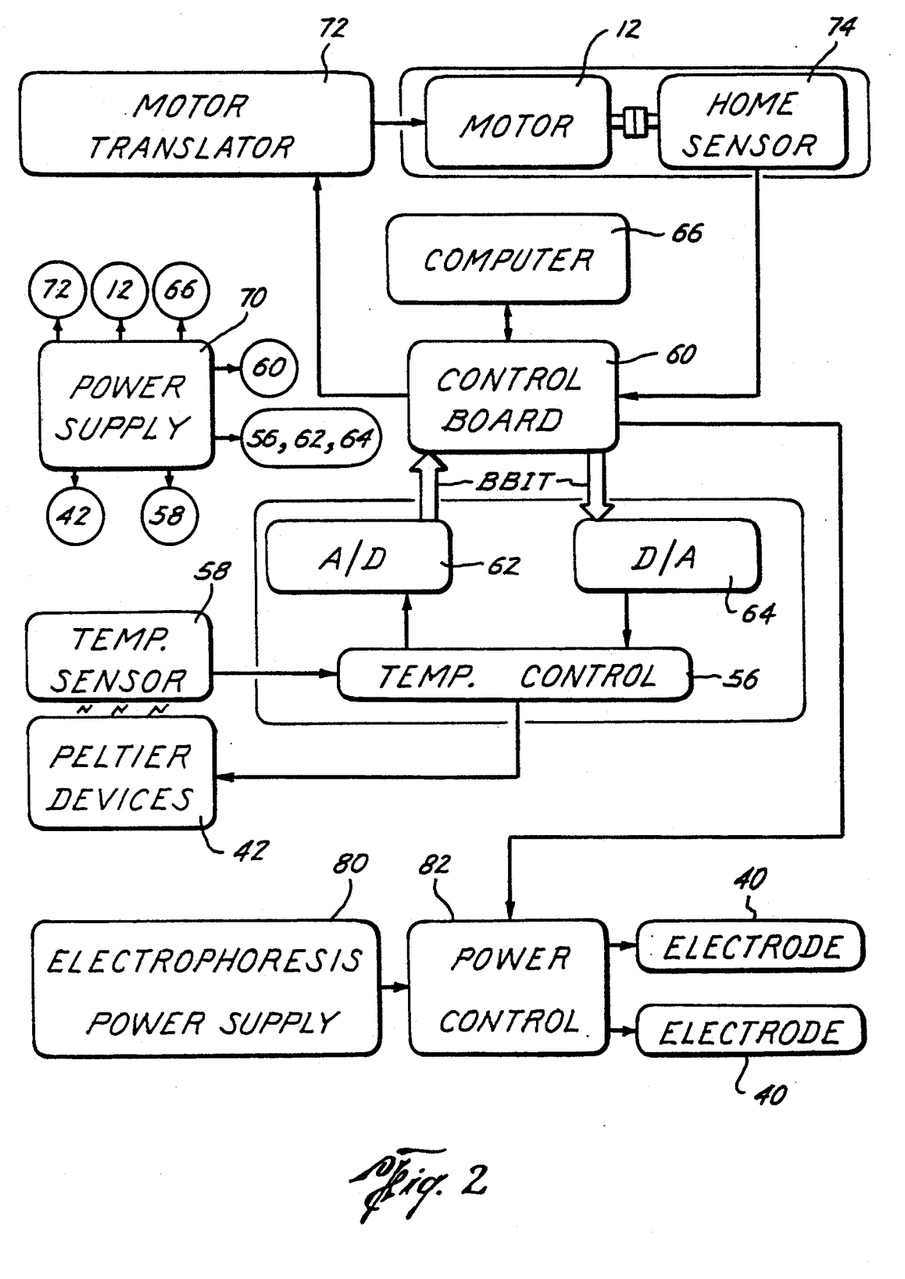
FIG. 2 is a block diagram showing the system for controlling electrical field and temperature according to the present invention.

The present invention utilizes user-programmable control of disk position, field magnitude, field polarity and temperature. Programming means such as a computer with keyboard entry is available to provide input control to apparatus 10. FIG. 2 illustrates a block diagram showing the system for controlling rotation (i.e., field direction), field magnitude, field polarity and temperature of device 10. Beginning with temperature control, Peltier devices or cells 42 are adapted for receiving electrical input from temperature control block 56. Peltier cells 42 are preferably sealed with silicon sealer to prevent accidental seepage of liquid (either buffer or condensed water from tanks 34) into the cell. Peltier cells are preferably manufactured by Melcor, Trenton, N.J., Model CP 2.0-127-06L. Upon receiving electrical current from temperature control 56, Peltier cells transfer heat from the adjacent solution to heat sinks 36. A temperature sensor may be used to communicate with the buffer solution to provide feed-back signals to temperature control 56. Sensor 58 is preferably made by National Semiconductor, Santa Clara, Calif., Model LM 35DZ. Temperature sensor 58 receives temperature readings from the buffer solution next to the disk 20 in the electrophoresis apparatus 10 and sends corrective signals to temperature control block 56 which then responds with the appropriate electrical signal to Peltier cell 42.

Temperature control block 56 functions to send output electric signal to cell 42 in response to temperature sensor input. The output of temperature sensor 58 is fed into an amplifier with a gain of 10. The amplifier, preferably manufactured by National Semiconductor, Santa Clara, Calif., Model LM 741N, is contained within the analog portion of the temperature controller 56. Also, within temperature controller 56 is a comparator which receives the amplified signal and which functions to compare the amplified signal with an operator-initiator reference signal sent through a digital-to-analog converter to the comparator. The comparator is preferably made by National Semiconductor, Model LM311N. When the temperature is above the reference, the output from the comparator forward biases a power MOSFET, rated at 40 amp, 50 volt, maximum on resistance of 0.028 Ohms (Motorola, Tempe, Ariz., Model MTH40N05) in series with the Peltier cell 42, thereby turning on the cooling of cell 42. To provide information for the control board, amplified signal from temperature sensor 58 is sent to an analogue to digital converter and is used for reporting. This signal could, however, also be used for control through the user's program. Temperatures are digitized in 8 bits; currently the range is 10° C. to 35.5° C. (0.1° C. resolution). This range, however, can be changed to accommodate any specific application.

Temperature control 56 is regulated by control board 60. Being digital-based, control board 60 interfaces with analog-based temperature control 56 via analog/digital converter 62 and digital/analog converter 64 as shown in FIG. 2. Control board 60 currently operates 8 bit data conversion devices but, can operate 16-bit data conversion devices if additional accuracy is needed.

Control board 60 functions to control temperature of the buffer solution simultaneous with control of the rotation of disk 20. For the introduction of user-programmable rotation upon disk 20, a computer 66 and keyboard are necessary. Control board 60 receives its program from a distal computer 66 and, once the program is entered, the keyboard and the computer are no longer necessary. At present, all programming is in BASIC ®. However, it is envisioned that any form of comparable programming language will be suitable as long as the desired rotation and temperature control are achieved. Use of a higher language simplifies programming. In case disk 20 is positioned improperly during rotation, an optical slit-containing-home-finding disk (30 in FIG. 1) is mounted on shaft 14 and a home-finding command is included in the program. The slit is monitored by an opto-interrupter 68 placed on stepping motor 12. Opto-interrupter 68 functions to determine when disk 20 is in a "home" position, in response to a home-finding command.

Computer 66 used for inputting and outputting signals to control board 60 may be any type of ASCII terminal having an RS-232 port. The control board which receives input from the computer and produces outputs into the computer, has an 8052-AH-BASIC microprocessor (8K byte BASIC ROM, a programmable pulse generator, built-in algorithm for programming EEPROMs and EPROMs) 8K byte of RAM, 8K byte of battery backed RAM, battery-backed real time clock and timer with resolution of 0.005 sec. 8K byte of ROM command extensions, 8K byte of EEPROM, 24 bits of programmable digital input-output, and an RS/232 printer port with a programmable Baud rate. A Micromint, Vernon, Conn., Model BCC-52 BASIC computer/controller is preferred as the control board of choice. However, any form of control board which performs the desired function can be utilized.

Control board 60 functions to receive computer 66 input and is driven by the power supply 70. Power supply 70 is a switching type with the following outputs: 12 volts, 19 amp for Peltier cell 42, the RS-232 port, the digital to analog converters 62 and 64, stepping motor 12, and temperature control block 56. Power supply 70 also provides −12 volts, 0.25 amps for the RS-232 port and the temperature control block. Still further, power supply 70 provides 5 volts and 1 amp for control board 60, temperature control block 56, motor translator 72 and home sensor 74. A preferable switching supply can be provided from Power One, Camarillo, Calif., Model SPL250-1012, modified with a switching invertor to provide conversion from 12 volts to −12 volts and a 5 volt linear regulator which converts 12 volts to 5 volts. Motor translator 72 functions to deliver 1 amp per phase in half-step sequence with a current-regulated bipolar output. Translator 72 is preferably a translator which can be built from schematic diagram found with data provided for the L298N full bridge device, page 263 of the Industrial and Peripheral ICS data book, SGS Thompson Microelectronics, Phoenix, Ariz.

Either independent from or associated with power supply 70 is an electrophoresis power supply 80 which produces sufficient voltage range, preferably between 40 volts to 300 volts, to supply electrical field between electrodes 40 shown in FIGS. 1 and 2. Electrophoresis power supply 80 is controlled by power control block 82. Power control 82 can control or change voltage magnitude, switch on or off, invert voltage polarity or pulse the voltage from power supply 80 to electrodes 40. Signals from control board 60 control or operate control block 82 to provide the desired voltage or current output.

Stepping motor 12 which drives rotating disk 20 is targeted for a minimum holding torque of 50 ounce-inches and 400 half-steps per revolution. To provide an absolute reference position, home-sensor 74 is connected to motor 12 and consists of an opto-interrupter and an opaque disk approximately 2.67 cm in radius with a 0.041 cm wide radial slit at the outer edge. The opaque disk 30 is mounted on shaft 14 of stepping motor 12 and the slit provided therein maintains a reference for the opto-interrupter mounted on the stepping motor. The opto-interrupter currently used is made by Optek Technology, Inc., Carrollton, Tex., Model OPB 10532.

Actual Results

Figure 3:
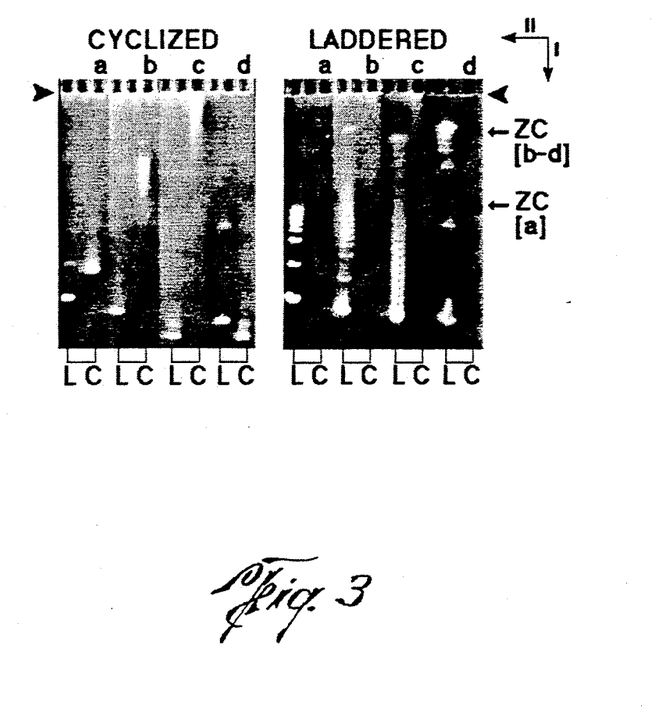
FIG. 3 is a plan view of molecular analysis conducted by rotating gel electrophoresis according to two embodiments of the present invention.

In preliminary experiments, to explore new modes, comparatively short pulses (5 second) of higher angle ($\alpha$) between pulse directions ($\alpha = 0.9\pi$ radians) are interspersed between longer pulses (90 seconds) of the original mode ($\alpha = 0.6\pi$ radian). The rationale for including shorter pulses was to disengage DNA that became tangled with the gel during the longer pulses. When tested with open circular DNA, the effectiveness of 18 shorter pulses after each of the longer pulses was discovered and is shown in FIG. 3. Electrophoresis of the illustrated samples shown in FIG. 3 was performed at 3 volts/cm, 20° C. in a 1.0% Seakem LE agarose gel (preferably manufactured by FMC Bioproducts, Rockland, Me.) cast in a 0.01M sodium phosphate, pH 7.4, 0.001M EDTA. The cyclized bacteriophage $\lambda$ DNA is cyclized by its cohesive ends by incubation at 3.2 $\mu$g DNA/ml in a 0.1M NaCl, 0.01M sodium phosphate, pH 7.4, 0.001M EDTA at 45° C. for 5–7 hours. The concatemerized bacteriophage DNA is joined end-to-end by the above procedure for cyclization, but applied to 100 $\mu$g DNA/ml for 2–3 hours. After electrophoresis, the gel was stained with 1 $\mu$g/ml ethidium and photographed. The directions of the first (I) and second (II) electrophoresis are indicated by the joined arrows and the origin of electrophoresis are indicated by the arrowheads on FIG. 3.

The monomeric open circular DNA, after identification by its immobility during a second dimension, invariant field electrophoresis (C lane in FIG. 3a cyclized), was observed to migrate as a sharp band even though the longer pulses alone yielded the expected broad distribution of open circular DNA at the origin (C lane in FIG. 3c cyclized). In FIG. 3a (cyclized), the band of monomeric open circular DNA was slightly further from the origin than the band of contaminating dimeric, linear DNA. The latter is in the L lane of FIG. 3a, cyclized). When the shorter pulses were the only pulses used, a band of monomeric open circular DNA (C lane of FIG. 3d, cyclized) was observed further from the origin than the band of monomeric linear DNA (L lane in FIG. 3d cyclized). To determine whether the effect on band sharpness depended on interspersing of the pulses in FIG. 3a (cyclized), the effect of delivering the pulses of FIG. 3a (cyclized), without interspersing (i.e. all longer pulses before all shorter pulses), was determined. The result was the broad pattern of FIG. 3c (cyclized), but translated away from the origin (C lane of FIG. 3b, cyclized). Thus, interspersion was necessary for the sharpening of the band of open circular DNA. That is, significant memory of previous pulse sequence has occurred.

On the same gels used in FIG. 3 (cyclized), the effect of interspersion of shorter and longer pulses was also determined for a linear $\lambda$ DNA ladder (FIG. 3, laddered). A result was the apparent movement of a zone of no resolution (zone of compression, or ZC) from its usual, origin/vicinal position (L lane in FIG. 3b–d, laddered) to a position closer to that of monomeric DNA (L lane in FIG. 3a laddered; a ladder is a collection of concatemers such that neighboring concatemers differ in length by a constant). Subsequent studies with longer ladders have revealed that the apparent zone of compression for FIG. 3a, laddered (ZC(a)) is attached to an extension of the ladder toward the origin from ZC(a). That is, the Applicants postulate that ZC(a) is a secondary zone of compression.

Foregoing description of the invention (including the apparatus, controlling mechanism and results obtained therefrom has been directed to a particular embodiment of the present invention. It will be apparent, however, to those skilled in the art that modifications and changes in both apparatus and method may be made without departing from the spirit and scope of the invention. For example, motor 12 may be actuated in a continuous or discontinuous mode of movement depending upon whether or not a continuously changing electric field-gel angle is needed. Further, the preferred solution between electrodes 40 can be any form of electrically conductive solution that has a fairly low conductivity. Still further, Peltier cell 42, holes 44, conductive sheet 46 and aluminum plate 48 can be of any dimension so long as they provide sufficient heat dissipation from the buffer solution to maintain a fairly close variance. Still further, rotatable disk 20 can be arranged in any position provided the disk is horizontal and does not leak buffer solution from the containment area once assembled within trough 22 of platform 24. Still further, programmable control of modes beyond merely disk rotation control, electrical source control (direction, magnitude and polarity) and buffer temperature control is envisioned by the applicants. Therefore, it is the Applicants' intention in the following claims to cover all such equivalent modifications and variations which fall within the true scope and spirit of the invention.

What is claimed is:

1. An apparatus for programmably controlling an electrophoretic device, comprising:
    a planar rotatable disk for supporting a horizontal gel containing at least on DNA particle;
    programmable rotating means connected to said disk for rotating said disk;
    at least two buffer holding tanks horizontally displaced from said rotatable gel bed, said tanks open at the top to provide electrically conductive buffer solution between said tanks and over said gel;
    programmable controlling means connected to said holding tanks for controlling the magnitude and polarity of the electric field placed between said tanks; and
    programmable Peltier means connected to said holding tanks for regulating the temperature of said buffer solution within said tanks and over said gel.

2. The apparatus as recited in claim 1, further comprising a means for containing a thin layer of said buffer solution upon the upper surface of said gel.

3. The apparatus as recited in claim 2, wherein said buffer solution is a phosphate-based solution.

4. The apparatus as recited in claim 1, wherein said rotating means comprises:
    a DC stepping motor mechanically coupled to said support; a home finder disk mechanically coupled to said support; and
    a control board electrically connected to said motor and said disk for controlling the speed, direction and duration of movement of the motor.

5. The apparatus as recited in claim 1, wherein said controlling means comprises:
    an electrode placed in each holding tank for receiving electrical inputs; and
    a control board electrically connected to each electrode for controlling magnitude, polarity and duration of electrical energy supplied to each said electrode.

6. The apparatus as recited in claim 1, wherein said Peltier means comprises:
    each said holding tank having an internal and external surface, said internal surface configured for containing said solution;
    a thermally conductive sheet having an internal and external surface, whereby said internal surface of said sheet is placed on the external surface of each said holding tank covering a hole in each said holding tank;
    whereby said internal surface of said plate is attached to the external surface of each said thermally conductive sheet;
    a Peltier cell having an internal and external surface, whereby said internal surface of said cell is attached to the external surface of each said plate;
    an aluminum heat sink having a planar inner surface attached to the external surface of said cell; and
    a control board electrically connected to each cell for inputting electrical input to the cell which, in response to the electrical input, the cell transfers heat to said heat sink.

7. The apparatus as recited in claim 1, wherein said Peltier means comprises:
    each said holding tank having an internal and external surface, said internal surface configured for containing said solution;
    a thermally conductive sheet having an internal and external surface, whereby said internal surface of said sheet is placed on the external surface of each said holding tank covering a hole in each said holding tank;
    a Peltier cell having an internal and external surface, whereby said internal surface of said cell is attached to the external surface of each said sheet;
    an aluminum heat sink having a planar inner surface attached to the external surface of said cell; and
    a control board electrically connected to each cell for inputting electrical input to the cell which, in response to the electrical input, the cell transfers heat to said heat sink.

8. The apparatus as recited in claim 1, wherein said Peltier means comprises:
    each said holding tank having an internal and external surface, said internal surface configured for containing said solution;
    a Peltier cell having an internal and external surface, whereby said internal surface of said cell is attached to the external surface of each said holding tank covering a hole in each said holding tank;
    an aluminum heat sink having a planar inner surface attached to the external surface of said cell; and
    a control board electrically connected to each cell for inputting electrical input to the cell which, in response to the electrical input, the cell transfers heat to said heat sink.

9. The apparatus as recited in claim 4, 5 or 8, wherein said control board is a microprocessor and memory-based controller with programmable pulse generator.

10. A method for multiplexing control of both electrical field and temperature during electrophoresis, comprising the steps of:
    placing particles onto a rotatable gel bed;

containing a buffer solution over said bed in communication with said particles;

applying a variable electric field to said bed at varying angles of incidence in response to programmed input; and drawing thermal energy from said solution in response to programmed electrical input.

11. The method as recited in claim 10, wherein the applying step comprises rotating said particles and buffer solution in a horizontal plane.

12. The method as recited in claim 10, wherein said drawing step comprises passing current through a Peltier device.

13. The method as recited in claim 10, further comprising multiplexing control of at least two gel beds, each bed containing said solution for receiving independently applied electrical field and independently drawn said thermal energy.

14. An apparatus for programmably controlling electrophoresis, comprising:

a substantially planar rotatable support member for supporting a medium adapted to hold at least one sample to be electrophoresis separated;

means for containing a buffer solution upon an upper surface of said rotatable support;

first programmable means for controlling an orientation of said rotatable support and for controlling a magnitude and polarity of an electric field acting upon said medium;

a thermoelectric chilling device for controllably chilling said buffer solution; and control means for controlling said programmable means and said thermoelectric chilling device, independent of one another.

15. An apparatus for programmably controlling electrophoresis comprising:

a substantially planar rotatable support member for supporting a medium adapted to hold at least one sample to be electrophoresis separated;

means for containing a buffer solution upon an upper surface of said rotatable support;

programmable means for controlling a magnitude and polarity of an electric field acting upon said medium;

a controllable stepping motor for controllably rotating said rotatable support member;

a Peltier device for controllably chilling said buffer solution; and control means for controlling said programmable means said Peltier device and said stepping motor, independent of one another.

* * * * *

UNITED STATES PATENT AND TRADEMARK OFFICE
CERTIFICATE OF CORRECTION

PATENT NO. : 5,185,071
DATED : February 9, 1993
INVENTOR(S) : Phillip Serwer, et. al.

It is certified that error appears in the above-identified patent and that said Letters Patent is hereby corrected as shown below:

Title page, column 2, the Assistant Examiner's last name is spelled incorrectly: delete --Stavsiak-- and insert "Starsiak".

In column 11, line 38, delete --on-- and insert "one".

In column 11, line 60, the phrase beginning "a home finder disk" should be on a separate line.

In column 12, line 15, insert "an aluminum plate having an internal and external surface" before "whereby".

In column 12, line 62, delete --8-- and insert "6".

In column 13, line 25, please delete --electrophoresis separated-- and insert "separated by electrophoresis".

In column 14, line 14, please delete --electrophoresis separated-- and insert "separated by electrophoresis".

Signed and Sealed this

Thirtieth Day of November, 1993

Attest:

BRUCE LEHMAN

Attesting Officer

Commissioner of Patents and Trademarks